(12) United States Patent
Hong et al.

(10) Patent No.: US 12,285,329 B2
(45) Date of Patent: *Apr. 29, 2025

(54) INTRAOCULAR LENSES HAVING ZONE-BY-ZONE STEP HEIGHT CONTROL

(71) Applicant: Alcon Inc., Fribourg (CH)

(72) Inventors: Xin Hong, Fort Worth, TX (US); Shinwook Lee, Arlington, TX (US)

(73) Assignee: Alcon Inc., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/587,687

(22) Filed: Feb. 26, 2024

(65) Prior Publication Data

US 2024/0189096 A1 Jun. 13, 2024

Related U.S. Application Data

(60) Continuation of application No. 17/663,748, filed on May 17, 2022, now Pat. No. 11,944,535, which is a
(Continued)

(51) Int. Cl.
*A61F 2/16* (2006.01)
*G02B 3/08* (2006.01)
*G02B 27/00* (2006.01)
*G02B 27/42* (2006.01)
*G02C 7/04* (2006.01)

(52) U.S. Cl.
CPC .......... *A61F 2/1656* (2013.01); *A61F 2/1616* (2013.01); *A61F 2/1618* (2013.01); *A61F 2/1654* (2013.01); *G02B 3/08* (2013.01); *G02B 27/0012* (2013.01); *G02B 27/4205* (2013.01); *G02C 7/04* (2013.01); *G02C 7/044* (2013.01); *A61F 2002/1683* (2013.01); *G02C 2202/20* (2013.01)

(58) Field of Classification Search
CPC .. A61F 2/1654; A61F 2/1656; G02C 2202/20
See application file for complete search history.

(56) References Cited

U.S. PATENT DOCUMENTS

| 5,016,977 A * | 5/1991 | Baude | A61F 2/164 |
| | | | 623/6.31 |
| 2002/0027712 A1* | 3/2002 | Soskind | G02B 27/4216 |
| | | | 359/565 |

(Continued)

*Primary Examiner* — Javier G Blanco
(74) *Attorney, Agent, or Firm* — PATTERSON + SHERIDAN, LLP

(57) ABSTRACT

A method and system provide an ophthalmic device. The ophthalmic device includes an ophthalmic lens having anterior surface, a posterior surface and at least one diffractive structure including a plurality of zones. The at least one diffractive structure is for at least one of the anterior surface and the posterior surface. Each zone includes at least one echelette having a least one step height. The step height(s) are individually optimized for each zone. To compensate chromatic aberration of eye from distance to a range of vision, a greater than $2\pi$ phase step height may be employed and the step height(s) folded by a phase, which is an integer multiple of two multiplied by $\pi$. Hence chromatic aberration of eye may be compensated to improve vision from distance to near.

16 Claims, 5 Drawing Sheets

Related U.S. Application Data continuation of application No. 17/073,896, filed on Oct. 19, 2020, now Pat. No. 11,364,112, which is a division of application No. 15/807,771, filed on Nov. 9, 2017, now Pat. No. 10,842,617.

(60) Provisional application No. 62/427,241, filed on Nov. 29, 2016.

(56) References Cited

U.S. PATENT DOCUMENTS

| | | | | |
|---|---|---|---|---|
| 2006/0164593 | A1* | 7/2006 | Peyghambarian | G02F 1/29 |
| | | | | 349/200 |
| 2010/0312336 | A1* | 12/2010 | Hong | A61F 2/1616 |
| | | | | 351/159.41 |
| 2011/0292335 | A1* | 12/2011 | Schwiegerling | G02B 5/1876 |
| | | | | 623/6.11 |
| 2011/0317237 | A1* | 12/2011 | Matsumoto | G02B 27/4205 |
| | | | | 359/238 |
| 2012/0113518 | A1* | 5/2012 | Ando | G02B 13/003 |
| | | | | 359/571 |

* cited by examiner

INTRAOCULAR LENSES HAVING ZONE-BY-ZONE STEP HEIGHT CONTROL

PRIORITY CLAIM

This application is a continuation of U.S. Non-Provisional patent application Ser. No. 17/663,748, filed on May 17, 2022, which is a continuation of U.S. Non-Provisional patent application Ser. No. 17/073,896, filed on Oct. 19, 2020, which is a divisional of U.S. Non-Provisional patent application Ser. No. 15/807,771, filed on Nov. 9, 2017, and claims the benefit of priority of U.S. Provisional Patent Application Ser. No. 62/427,241, filed on Nov. 29, 2016, and titled "INTRAOCULAR LENSES HAVING ZONE-BY-ZONE STEP HEIGHT CONTROL," whose inventors are Xin Hong and Shinwook Lee, which is hereby incorporated by reference in its entirety as though fully and completely set forth herein.

FIELD

The present disclosure relates generally to intraocular lenses and more particularly to intraocular lenses having zone by zone step height control.

BACKGROUND

Intraocular lenses (IOLs) are implanted in patients' eyes either to replace a patient's lens or to complement the patient's lens. The IOL may be implanted in place of the patient's lens during cataract surgery. Alternatively, an IOL may be implanted in a patient's eye to augment the optical power of the patient's own lens.

Some conventional IOLs are single focal length IOLs, while others are multifocal IOLs. Single focal length IOLs have a single focal length or single power. Objects at the focal length from the eye/IOL are in focus, while objects nearer or further away may be out of focus. Although objects are in perfect focus only at the focal length, objects within the depth of focus (within a particular distance of the focal length) are still acceptably in focus for the patient to consider the objects in focus. Multifocal IOLs have at least two focal lengths. For example, a bifocal IOL has two focal lengths for improving focus in two ranges: a distance focus corresponding to a larger focal length and a near focus corresponding to a smaller focal length. Thus, a patient's distance vision and near vision may be improved. Trifocal IOLs have three focuses: a far focus for distance vision, a near focus for near vision and an intermediate focus for intermediate vision. The intermediate focus has an intermediate focal length between that of the near and far focuses. Multifocal IOLs may improve the patient's ability to focus on distant and nearby objects.

In order to fabricate a conventional IOL, optical design software is generally employed. The desired focal lengths and locations of zones on the lens surface are provided. Given these inputs, the entire lens is analytically optimized using the optical software. Stated differently, the diffraction structures for multiple zones are simultaneously optimized using analytic tools. As a result, an IOL may be provided.

Although useful in addressing optical conditions, IOLs may suffer from various drawbacks such as longitudinal chromatic aberration and/or a limited depth of focus. Different colors of light have different wavelengths and, therefore, different frequencies. As a result, the IOL focuses light of different colors at different distances from the lens. The IOL may be unable to focus light of different colors at the patient's retina. The polychromatic image contrast for the IOL may be adversely affected. In addition, the depth of focus of the IOL may not be as large as desired. The patient's vision for ranges further from the focal length may be adversely affected. Consequently, an extended depth of focus (EDOF) may be desired.

Accordingly, what is needed is a system and method for improving IOLs.

SUMMARY

A method and system provide an ophthalmic device. The ophthalmic device includes an ophthalmic lens having anterior surface, a posterior surface and at least one diffractive structure including a plurality of zones. The at least one diffractive structure is for at least one of the anterior surface and the posterior surface. Each zone includes at least one echelette having a least one step height. The step height(s) are individually provided for each zone. The at least one step height is also folded by a phase, which is an integer multiple of two multiplied by π.

The lens may having the diffractive structure(s) described above may have reduced chromatic aberration and greater EDOF. As a result, performance may be improved.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

DETAILED DESCRIPTION

The exemplary embodiments relate to ophthalmic devices such as IOLs and contact lenses. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. For example, the method and system are described primarily in terms of IOLs. However, the method and system may be used with contact lenses. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown, but is to be accorded the widest scope consistent with the principles and features described herein.

A method and system provide an ophthalmic device. The ophthalmic device includes an ophthalmic lens having anterior surface, a posterior surface and at least one diffractive structure including a plurality of zones. The diffractive structure(s) are for at least one of the anterior surface and the posterior surface. Each zone includes at least one echelette having a least one step height. The step height(s) are individually determined for each zone. The step height(s) are also folded by a phase, which is an integer multiple of two multiplied by T.

Figure 1A:
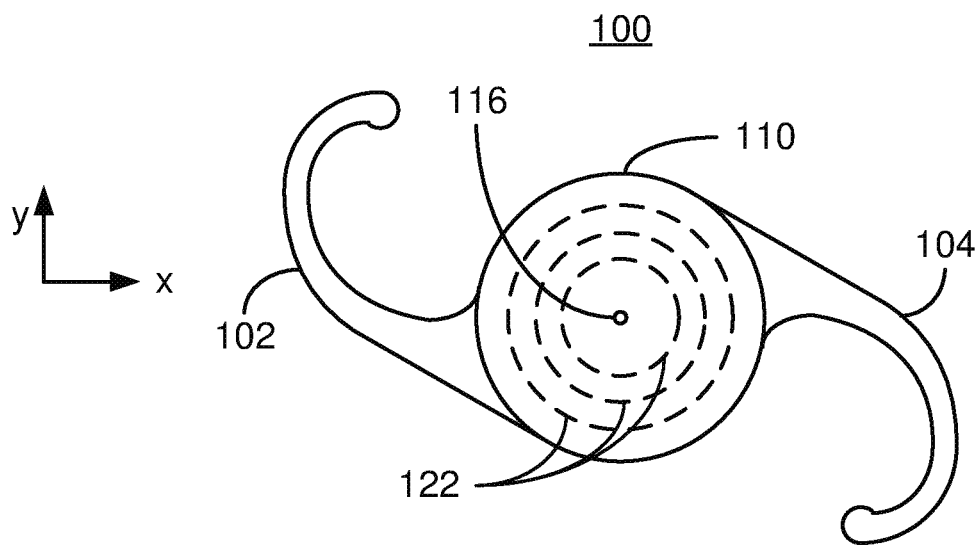
FIGS. 1A and 1B depict a plan and side views of an exemplary embodiment of a multifocal ophthalmic device that includes individually optimized zones and phase folding.
Figure 1B:
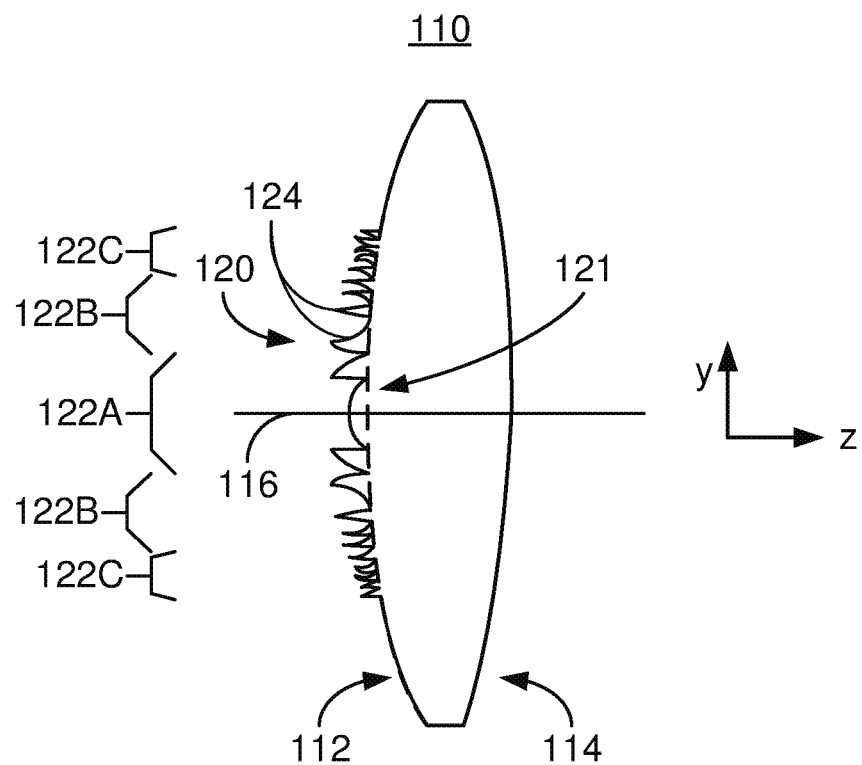

FIGS. 1A-1B depict an exemplary embodiment of an ophthalmic device 100 that may be used as an IOL. FIG. 1A depicts a plan view of the ophthalmic device 100, while FIG. 1B depicts a side view of the ophthalmic lens 110. For clarity, FIGS. 1A and 1B are not to scale, for explanatory purposes only and depict only some features. The ophthalmic device 100 includes an ophthalmic lens 110 (herein after "lens") as well as haptics 102 and 104. The lens 110 may be made of a variety of optical materials including but not limited to one or more of silicone, a hydrogel, an acrylic and AcrySof®. Haptics 102 and 104 are used to hold the ophthalmic device 100 in place in a patient's eye (not explicitly shown). In other embodiments, other mechanism(s) might be used to retain the ophthalmic device in position in the eye. Thus, the haptics 102 and/or 104 might be omitted. For clarity, the haptics are not depicted in the remaining drawings. Although the lens 110 is depicted as having a circular cross section in the plan view of FIG. 1A, in other embodiments, other shapes may be used. Although described in the context of an IOL, the lens 110 may be a contact lens. In such a case, the haptics 102 would be omitted and the lens 110 sized and otherwise configured to reside on the surface of the eye.

The lens 110 may, but need not, be a multifocal lens. The lens 110 has an anterior surface 112 a posterior surface 114 and an optic axis 116. The lens is also characterized by a diffractive structure 120 and a base curvature 121. The lens 110 may provide a base power, astigmatism correction and/or other vision correction(s). The lens 110 may be aspheric and/or toroidal, have the same or different base curvatures on the surfaces 112 and 114 and/or other characteristics that are not shown or discussed in detail for simplicity. Although one diffractive structure 120 is shown on the anterior surface 112, the diffractive structure 120 might be located on the posterior surface 114. In still other embodiments, diffractive structures may be located on the anterior surface 112 and the posterior surface 114. Such diffractive structures may be the same or different. The diffractive structure 120 may, but need not, be partial aperture diffractive structure. Further, although shown as a physical diffractive structure, in other embodiments, the diffractive structure 120 may be formed by a change in the index of refraction of the lens 110.

The diffractive structure 120 may provide a single focal length or multiple focal lengths. In some embodiments, the diffractive structure 120 is used to provide a bifocal (two focal lengths for near and distance vision) lens 110. In other embodiments, the diffractive structure 120 may provide a trifocal (three focal lengths for near, intermediate and distance vision) lens 110. A quadrifocal or other multifocal lens might also be provided. The diffractive structure 120 may be configured for particular wavelength(s). For example, different zones 111 of the diffractive structure 120 may be configured for light of different wavelengths. Alternatively, the diffractive structure 120 may be designed for light of a single wavelength.

The diffractive structure 120 includes multiple zones 122A, 122B and 122C (collectively zones 122) corresponding to different ranges in distance perpendicular to the optic axis 116 (i.e. different radii). Although three zones 122 are shown, the lens 110 may have another number of zones. A zone 122A, 122B and/or 122C is a circle or an annular ring along the surface from a minimum radius to a maximum radius from the optic axis 116. For example, in some embodiments, the diffractive structure 120 may have ring diameters for the zones 122 set by the Fresnel diffractive lens criteria. Alternatively, other criteria may be used to determine the size and location of each of the zones 122.

Each of the zones 122 includes steps, or echelettes 124. The echelettes 124 have step heights that correspond to phase differences. The step height of an echelette 124 is the physical step height (h) multiplied by the difference in index of refraction between the lens 110 and the surrounding media ($\Delta n$). In other words, the step height=$h \cdot \Delta n$. The phase difference, $\phi$, for an echelette 124 is proportional to the step height divided by the wavelength, $\lambda$. More specifically, $\phi=(2 \cdot \pi \cdot h \cdot \Delta n)/\lambda$. A phase difference of $2\pi$ thus corresponds to one wavelength in step height. Thus, the terms step height and phase are considered to be effectively synonymous herein.

The echelettes 124 of one or more of the zones 122 are individually optimized. Stated differently, one or more of the characteristics of the echelettes 124 for a zone 122A, 122B and/or 122C are determined for that zone 122A, 122B and/or 122C, respectively, independent of the characteristics of the echelettes 124 in another zone. In some embodiments, the step heights (phases) of the echelettes 124 in the zones 122 are separately determined on a zone-by-zone basis. Thus, the step height(s) for each zone 122A, 122B and/or 122C are determined independently of the step height(s) for another zone. In other embodiments, additional or other characteristics of the echelettes 124 may be separately configured on a zone-by-zone basis. For example, the spacing between echelettes 124 may also be independently controlled for each zone 122.

The characteristic(s) of the echelettes 124 for each of the zones 122A, 122B and 122C may be independently optimized based on selected criteria. For example, particular focal length(s) for the lens 110, target focus positions, location and amount of constructive interference, target phases and/or other criteria may be used to separately determine the step height(s) for each of the zones 122. These criteria may change between the zones 122. In other embodiments, these criteria may be the same for each of the zones 122. Because of the locations of the zones 122 differ, different step heights may be determined for different zones 122 even if the criteria stay the same.

In some embodiments, the phases (i.e. step heights) for the echelettes 124 in each zone can be individually optimized such that each of the zones 122 constructively interferes at different target positions. As a result, the depth of focus may be improved for the lens 110. In some instances, a relatively uniform through-focus may be achieved. Each of the zones 122 may be separately optimized for one or more of the focal lengths of a multifocal lens 110. For example, each of the zones 122 may be optimized to provide different intermediate focal lengths. Thus, the depth of focus may be improved.

Although discussed in the context of independently configuring the echelettes 124 for each of the zones 122, one of ordinary skill in the art will recognize that not all of the zones 122 must be so configured. For example, in some embodiments, echelettes 124 for only the zones 122A and 122B might be separately determined. In other embodiments, echelettes 124 for only the zones 122A and 122C may be separately configured. In still other embodiments, characteristics of the echelettes 124 for only the zones 122B and 122C might be independently determined. In other embodiments, all of the zones 122 of the lens 110 might be separately manipulated. Thus, the specific zones 122 having echelettes 124 that are independently manipulated may change between embodiments.

The zones 122 may undergo phase folding in addition to separate, zone-by-zone optimization of the step height(s). The individually determined step height(s) for one or more of the zones 122 may be large. The corresponding phases may exceed 2·π. In some cases, the optimized step heights may correspond to phases of at least 3·π, at least 4·π, or more. Therefore, the step heights are folded by a phase of 2·π·n, where n is a positive integer, if the step height is sufficiently large. In some embodiments, the step heights of the echelettes 124 may be reduced to provide a maximum phase of 2·π. Thus, in addition to being separately controlled, the step heights of the echelettes 124 of each zone 122A, 122B and/or 122C are folded. This reduction in the step height may reduce the light interference from light far from the optic axis 116. The phase folding may also provide a negative dispersion that may partially or wholly compensate for the positive dispersion of the material from which the lens 110 is formed.

The ophthalmic lens 110 may have improved performance. The ophthalmic lens 110 may be a multifocal lens. The ophthalmic device 100 may be used to treat conditions such as presbyopia. Other conditions such as astigmatism may be treated and performance of the lens 110 may be improved through the use of the base curvature 121, asphericity of the lens 110, toricity of the lens 110, apodization of the echelettes 122 and other characteristics of the lens. In addition, the lens 110 may have improved EDOF as well as reduced chromatic aberration. Separately controlling the step height(s) of the echelettes 124 in each of the zones 122 may allow the image to be sufficiently in focus over a larger range of distances. Thus, depth of focus may be improved. Because the echelettes are also phase folded, chromatic aberrations introduced by the lens 110 may be compensated for. This use of the superzone and phase wrapping may compensate a chromatic aberration of the eye through strong negative dispersion of a diffractive lens and correcting chromatic aberration from distance to a range of vision. Thus, depth of focus may be increased while a more achromatic lens 110 may be provided. Consequently, performance may be improved.

Figure 2:
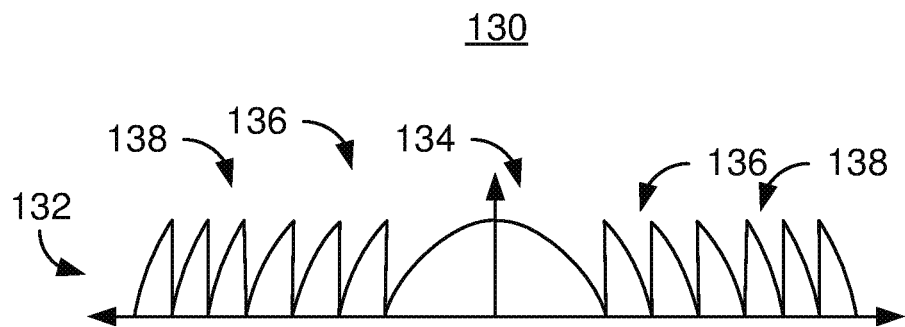
FIG. 2 depicts an exemplary embodiment of a sag profile for a diffractive structure of a multifocal ophthalmic lens that includes individually optimized zones and phase folding.
Figure 3A:
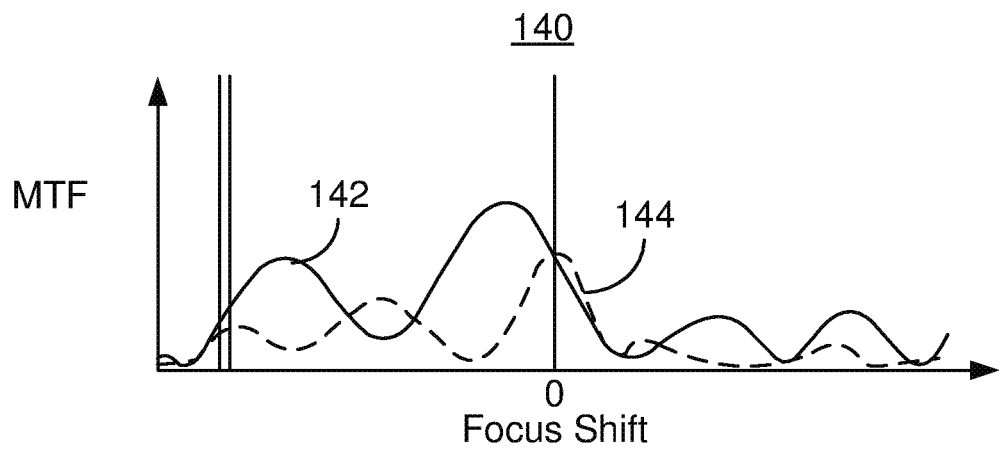
FIGS. 3A-3B depict exemplary embodiments of the intensity versus focus shift for a multifocal ophthalmic lens that includes individually optimized zones and phase folding.
Figure 3B:
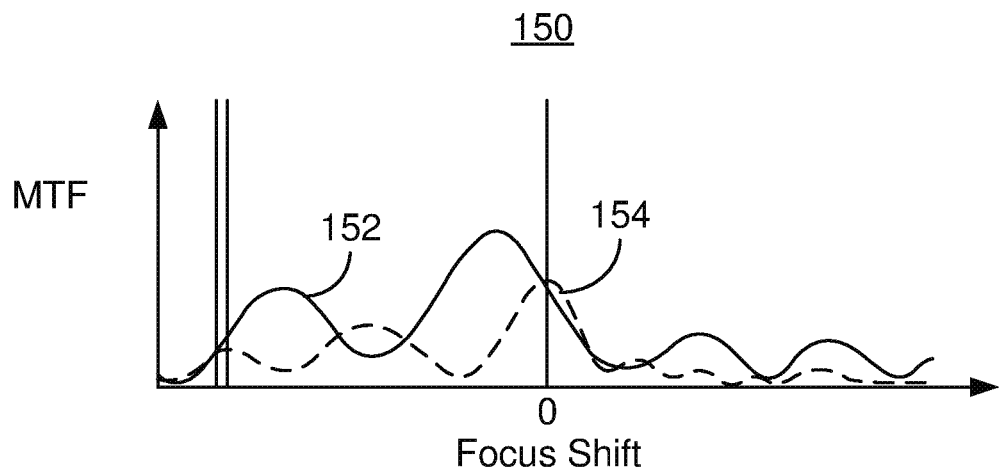

The benefits of the ophthalmic lens 110 may be better understood with respect to certain embodiments. FIG. 2 depicts a sag profile 130 for another exemplary embodiment of a diffractive structure that includes individually controlled zones and phase folding. Thus, the sag profile 130 and diffractive structure 130 are referred to interchangeably. The diffractive structure 130 may take the place of the diffractive structure 120 in the lens 110. The sag profile 130 indicates that there are zones 134, 136 and 138, each of which includes one or more echelettes 132. FIGS. 3A and 3B are graphs 140 and 150, respectively, depicting exemplary embodiments of the monochromatic and photopic intensity, respectively, versus focus shift for a trifocal lens 110 made with the diffractive structure 130. The curves 142 and 152 are for one set of line pairs, while the curves 144 and 154 are for another set of line pairs having twice the frequency. FIGS. 2-3B are not to scale and for explanatory purposes only.

As can be seen in the graphs 140 and 150, the thru focus modulation transfer function (MTF) curves 142/152 and 144/154 are shifted due to separate, zone-by-zone control of the step heights of the echelettes 132 in the sag profile 130. This shift compensates for valleys in the MTF curves. Thus, the depth of focus for a lens incorporating the sag profile 130 has been improved. Because of phase folding of the diffractive structure 130, chromatic aberration may also be compensated for. As a result, the MTF is shown as dropping by a smaller amount over the extended distance in the graphs 140 and 150. Thus, the depth of focus and achromatization of the lens 110 having the sag profile 130 may be improved. The performance of the lens 110 employing a diffractive structure having the sag profile 130 may be enhanced.

Figure 4:
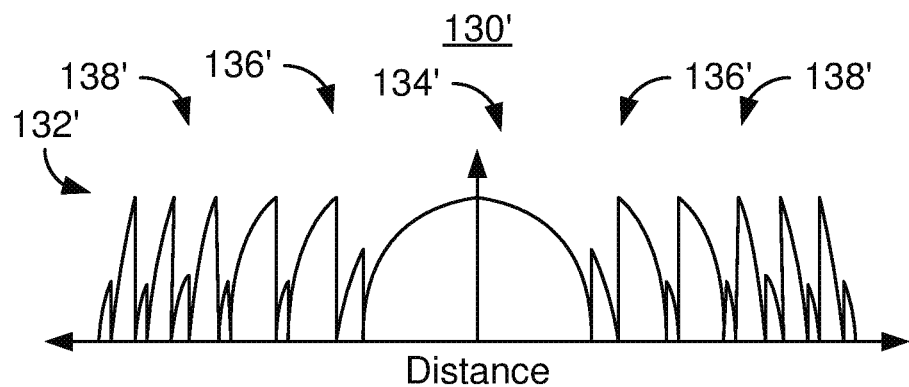
FIG. 4 depicts an exemplary embodiment of sag profile for a diffractive structure of an ophthalmic lens having an extended depth of focus and that includes individually optimized zones and phase folding.
Figure 5A:
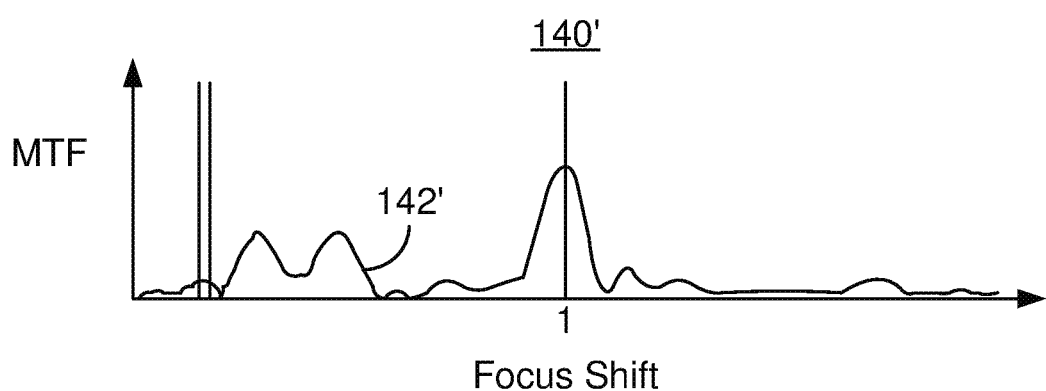
FIGS. 5A-5B depict exemplary embodiments of the intensity versus focus shift a lens that includes individually optimized zones and phase folding.
Figure 5B:
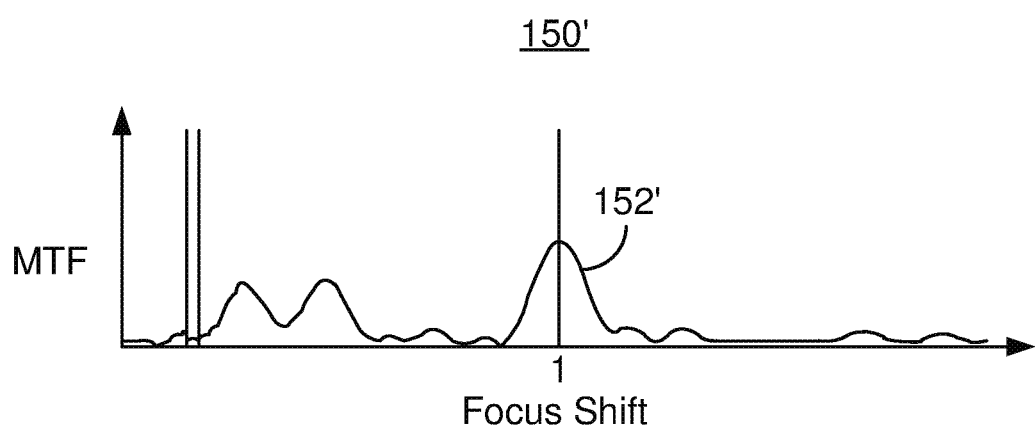

FIG. 4 depicts a sag profile 130' for another exemplary embodiment of a diffractive that includes individually controlled zones and phase folding. Thus, the sag profile 130' and diffractive structure 130' are referred to interchangeably. The diffractive structure 130' may take the place of the diffractive structure 120 in the lens 110. The sag profile 130' indicates that there are zones 134', 136' and 138', each of which includes one or more echelettes 132'. FIGS. 5A and 5B are graphs 140' and 150', respectively, depicting exemplary embodiments of MTF versus focus shift for a trifocal lens 110 made with the diffractive structure 130'. The curve 142' depicts the monochromatic MTF, while the curve 152' is for photopic MTF. FIGS. 4-5B are not to scale and for explanatory purposes only. In the embodiment shown, the near power may be set by adding power to the lens 110, while the intermediate power may be provided by separate, zone-by-zone optimization of the step heights for the sag profile 130'. In addition, the step height for the echelettes 132' may be folded by an integer multiple of 2·π. For example, the maximum phase corresponding to the echelettes 132' may be 2·π.

As can be seen in the graphs 140' and 150', the curves 142' and 152' provide for an intermediate focus. This is due to separate control of the echelette step heights for the zones 134', 136' and 138' as shown in the sag profile 130'. Thus, the depth of focus has been improved. Because of phase folding of the diffractive structure 130', chromatic aberration may also be compensated for the depth of focus and achromatization of the lens 110 having the sag profile 130' may be improved. Thus performance of the lens 110 employing a diffractive structure having the sag profile 130 may be enhanced.

Figure 6:
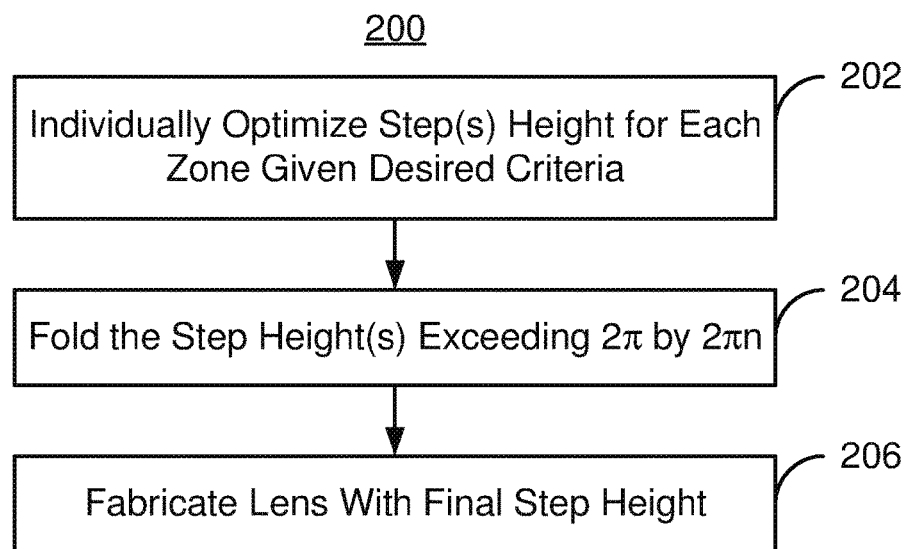
FIG. 6 is flow chart depicting an exemplary embodiment of a method for fabricating an ophthalmic device that includes individually optimized zones and phase folding.
Figure 7:
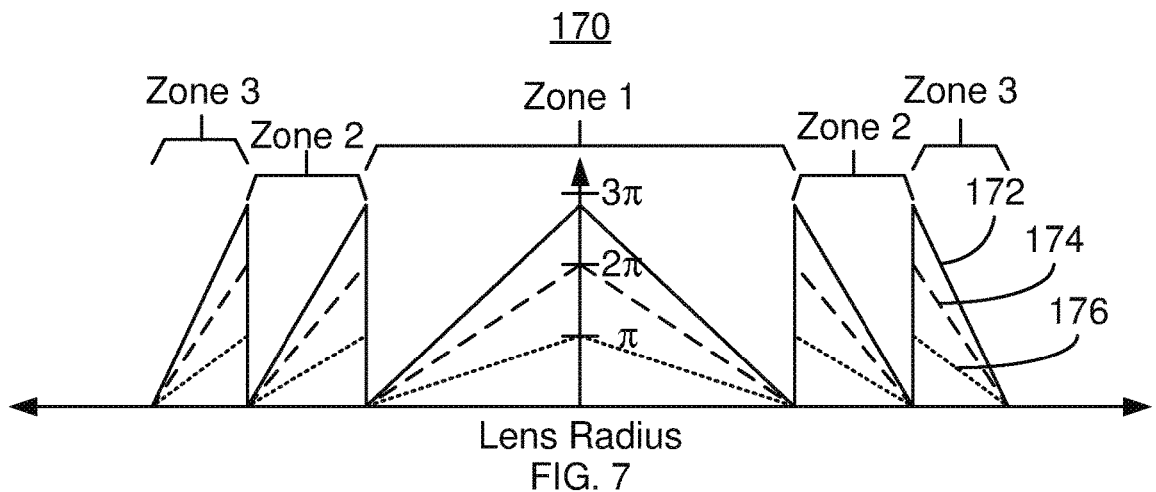
FIG. 7 depicts an exemplary embodiment of a sag profile for diffractive structure during design that includes individually optimized zones.
Figure 8:
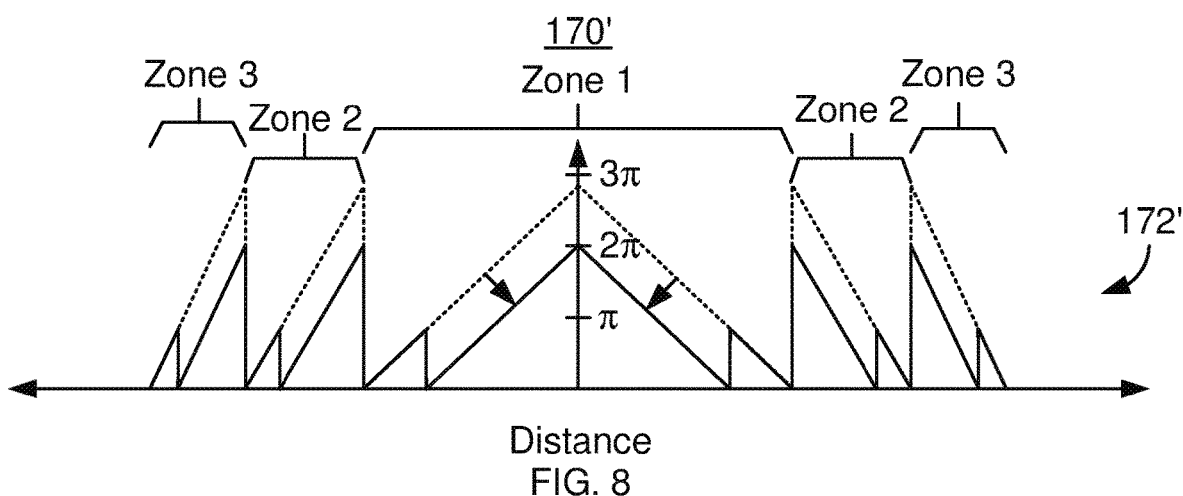
FIG. 8 depicts an exemplary embodiment of a sag profile for diffractive structure during design that includes individually optimized zones and phase folding.

FIG. 6 is an exemplary embodiment of a method 200 for providing a multifocal diffractive lens having reduced chromatic aberration. For simplicity, some steps may be omitted, interleaved, and/or combined. FIGS. 7 and 8 depict sag profiles 170 and 170' for a lens designed using the method 200. The sag profiles 170 and 170' are for explanatory purposes only and are not intended to represent specific devices. Referring to FIGS. 6-8, the method 200 may be used to provide the ophthalmic device 100 and lens 110 and diffractive structure 120. However, the method 200 may be used with one or more other diffractive structure 130 and/or 130" and/or an analogous ophthalmic device.

The method 200 may be executed using a system including one or more processors and a memory. The one or more processors may be configured to execute instructions stored in the memory to cause and control some or all of the process(es) set forth in the drawings and described herein. As used herein, a processor may include one or more microprocessors, field-programmable gate arrays (FPGAs), controllers, or any other suitable computing devices or resources, and memory may take the form of volatile or non-volatile memory including, without limitation, magnetic media, optical media, random access memory (RAM), read-only memory (ROM), removable media, or any other suitable memory component. Memory may store instructions for programs and algorithms that, when executed by a processor, implement the functionality described herein with respect to any such processor, memory, or component that includes processing functionality. Further, aspects of the method and system may take the form of an entirely hardware embodiment, an entirely software embodiment (including firmware, resident software, micro-code, etc.) or an embodiment combining software and hardware aspects. Furthermore, aspects of the method and system may take the form of a software component(s) executed on at least one processor and which may be embodied in one or more computer readable medium(s) having computer readable program code embodied thereon.

The diffractive structure for the lens 110 is designed using steps 202 and 204. The step height(s) for the echelettes are determined by individually configuring each of the zones, via step 202. Step 202 may be performed analytically, using processor(s) that executes instructions. For example, the desired target focus locations, focal lengths, zone locations and/or other criteria may be provided as inputs to software for designing optical gratings and an optimization performed. As a result, optimized step heights that correspond to optimized phases are independently determined for each zone of some or all of the diffractive structure being formed. Although termed an optimization process, one of ordinary skill in the art will recognize that the step height(s) determined may not be optimal for every possible set of criteria used. Instead, the optimization process is one that can use analytic tools to determine the step height based on criteria provided by the user. FIG. 7 is a graph 170 depicting a simplified, superzone sag profile 172 resulting from step 202. The profile 172 is simplified as a linear profile but more generally would be curved. Thus, the sag profile 172 has three zones. The optimization process has resulted in echelettes for the sag profile 172 having large optimized step heights. The sag profile 172 includes first and second orders as the main orders. For comparison, a sag profile 174 for a monofocal Fresnel lens and a sag profile 176 for a bifocal diffractive lens are shown. The sag profile 174 utilizes the first order, while the sag profile 176 utilizes the zeroth and first orders. The phases corresponding to the echelettes of the sag profile 172 have optimized phases that are greater than $2 \cdot \pi$.

The optimized step heights are folded if the optimized phases exceed $2 \cdot \pi$, via step 204. The phase used in folding is a positive integer multiplied by $2 \cdot \pi$. In the embodiment shown, all of the zones have large optimized step heights. Consequently, the optimized step heights for all zones are folded. In another embodiment, the optimized step height for only some zones may be folded. FIG. 8 is a graph 170' depicting the resultant simplified sag profile 172' after folding has been performed. The profile 172' is simplified as a linear profile but more generally would be curved. Thus, the echelettes of the sag profile 172' all have reduced phases. Also shown with dashed lines is the original curve 172 and the direction the sag profile 172 is moved to form the final curve 172'

The lens(es) 110 are fabricated, via step 206. Thus, the desired diffractive structure 120 having the sag profile 170' may be formed. The diffractive structure(s) 120, 130, 130' and/or an analogous diffractive structure may be provided and the benefits thereof achieved.

Figure 9:
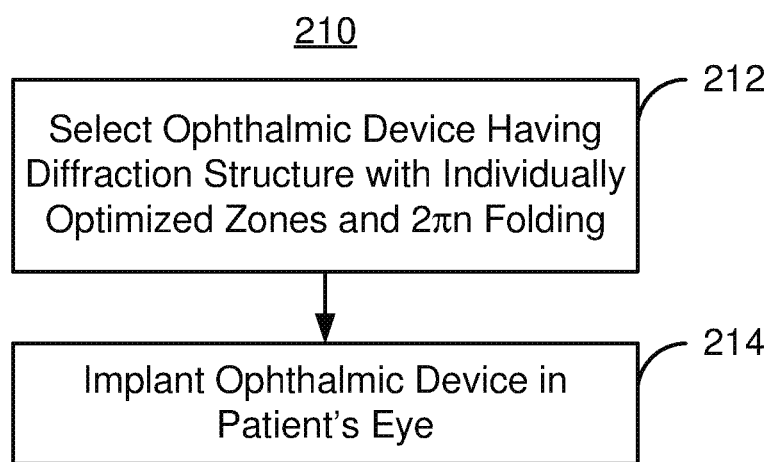
FIG. 9 is flow chart depicting an exemplary embodiment of a method for utilizing an ophthalmic device including a multifocal lens that may have reduced chromatic aberration.

FIG. 9 is an exemplary embodiment of a method 210 for treating an ophthalmic condition in a patient. For simplicity, some steps may be omitted, interleaved, and/or combined. The method 210 is also described in the context of using the ophthalmic device 100 and ophthalmic lens 110. However, the method 210 may be used with one or more of diffractive structures 130, 130', 170' and/or an analogous diffractive structure.

An ophthalmic device 100 for implantation in an eye of the patient is selected, via step 212. The ophthalmic device 100 includes an ophthalmic lens 110 having a diffractive structure 120 that has individually optimized zones 122 that have also been folded. A lens having a diffractive structure 120, 130, 130', 170' and/or an analogous diffractive structure may thus be selected for use.

The ophthalmic device 100 is implanted in the patient's eye, via step 204. Step 204 may include replacing the patient's own lens with the ophthalmic device 100 or augmenting the patient's lens with the ophthalmic device. Treatment of the patient may then be completed. In some embodiments implantation in the patient's other eye of another analogous ophthalmic device may be carried out.

Using the method 200, the diffractive structure 120, 130, 130', 170' and/or analogous diffractive structure may be used. Thus, the benefits of one or more of the ophthalmic lens 110 may be achieved.

A method and system for providing an ophthalmic device have been described. The method and systems have been described in accordance with the exemplary embodiments shown, and one of ordinary skill in the art will readily recognize that there could be variations to the embodiments, and any variations would be within the spirit and scope of the method and system. Accordingly, many modifications may be made by one of ordinary skill in the art without departing from the spirit and scope of the appended claims.

We claim:

1. An ophthalmic lens having at least one focal length, the ophthalmic lens comprising:
   at least one diffractive structure including a plurality of zones, each of the plurality of zones including at least one echelette having at least one step height, the at least one step height of each of the plurality of zones being individually determined and optimized for each zone of the plurality of zones;

wherein at least one of the plurality of zones includes an optimized step height greater than $2\pi$ that is subsequently folded by a phase, the phase being an integer multiple of two multiplied by $\pi$, wherein, after folding by the phase, the optimized step height is not more than two multiplied by $\pi$.

2. The ophthalmic lens of claim 1, wherein the ophthalmic lens comprises a contact lens or an intraocular lens (IOL).

3. The ophthalmic lens of claim 1, wherein the at least one focal length includes a plurality of focal lengths such that the ophthalmic lens is a multifocal lens.

4. The ophthalmic lens of claim 3, wherein each zone is individually optimized for a portion of the plurality of focal lengths.

5. The ophthalmic lens of claim 3, wherein each zone is individually optimized for the plurality of focal lengths.

6. The ophthalmic lens of claim 1, wherein the at least one step height includes a plurality of step heights.

7. The ophthalmic lens of claim 1, wherein each zone is individually optimized for one of a plurality of target positions.

8. The ophthalmic lens of claim 7, wherein each zone constructively interferes at a different target position of the plurality of target positions.

9. An ophthalmic lens having at least one focal length, the ophthalmic lens comprising:
  at least one diffractive structure including a plurality of zones, each of the plurality of zones including at least one echelette having at least one step height, the at least one step height of each of the plurality of zones being individually determined and optimized for each zone of the plurality of zones;
  wherein a particular echelette in a particular one of the plurality of zones has an optimized step height that exceeds $2\pi$ and the diffractive structure includes a first echelette and a second echelette to represent the particular echelette, the first echelette having a step height of $2\pi$ and the second echelette having a step height of a difference between the optimized step height and $2\pi$,
  wherein the difference between the optimized step height and $2\pi$ is achieved by folding the optimized step height by a phase,
  wherein, after folding the optimized step height by the phase, the step height of the second echelette is not more than two multiplied by $\pi$.

10. The ophthalmic lens of claim 9, wherein the ophthalmic lens comprises a contact lens or an intraocular lens (IOL).

11. The ophthalmic lens of claim 9, wherein the at least one focal length includes a plurality of focal lengths such that the ophthalmic lens is a multifocal lens.

12. The ophthalmic lens of claim 11, wherein each zone is individually optimized for a portion of the plurality of focal lengths.

13. The ophthalmic lens of claim 11, wherein each zone is individually optimized for the plurality of focal lengths.

14. The ophthalmic lens of claim 9, wherein the at least one step height includes a plurality of step heights.

15. The ophthalmic lens of claim 9, wherein each zone is individually optimized for a plurality of target positions.

16. The ophthalmic lens of claim 15, wherein each zone constructively interferes at a different target position of the plurality of target positions.

* * * * *